United States Patent [19]

Moore

[11] 4,260,624
[45] Apr. 7, 1981

[54] FUNGICIDAL 2-SUBSTITUTED-3-OXA-3A LAMBDA 4,4-DITHIA-6-CHLORO-1,5-DIAZAPENTA-LENE

[75] Inventor: Joseph E. Moore, Richmond, Calif.

[73] Assignee: Chevron Research Company, San Francisco, Calif.

[21] Appl. No.: 117,152

[22] Filed: Jan. 31, 1980

[51] Int. Cl.³ .................... A01N 43/82; A01N 43/90; C07D 513/04
[52] U.S. Cl. ................................. 424/270; 260/464; 260/465.4
[58] Field of Search .................... 548/122; 424/270

[56] References Cited

U.S. PATENT DOCUMENTS

| | | | |
|---|---|---|---|
| 3,726,891 | 4/1973 | Pilgram et al. | 548/129 |
| 4,179,441 | 12/1979 | Moore | 548/122 |

Primary Examiner—Alton D. Rollins
Attorney, Agent, or Firm—D. A. Newell; T. G. DeJonghe; L. S. Squires

[57] ABSTRACT

Fungicidal oxadithiadiazapentalenes of the formula

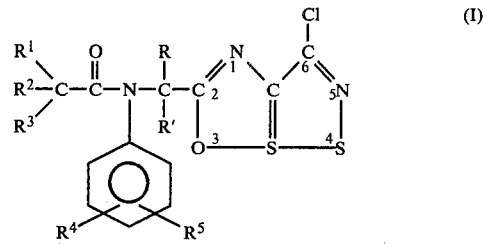

wherein R and R' are independently hydroxy or lower alkyl; $R^1$ is hydrogen or lower alkyl; $R^2$ and $R^3$ are each, independent of the other, hydrogen, halogen, alkenyl, hydroxy, hydroxyalkenyl, alkoxy, alkoxyalkyl, alkoxyalkenyl, alkylthio, or haloalkyl having from 1 to 3 carbon atoms and from 1 to 4 halogen atoms or $R^2$ and $R^3$ together are alkylidiene, alkoxyalkenyl or together with the carbon atom to which they are joined form a cycloalkyl group; and $R^4$ and $R^5$ are each independent of the other hydrogen, alkyl, alkoxy, halogen, haloalkyl, nitro, cyano, or dialkylamino. The compounds can be prepared by reacting sulfur chloride with the appropriate substituted N-cyanoalkylenecarboxyamide corresponding to the substituent desired at the 2-position of the compounds. The compounds are useful for controlling plant fungus; especially Grape Downy Mildew fungus and Tomato Late Blight fungus.

28 Claims, No Drawings

FUNGICIDAL 2-SUBSTITUTED-3-OXA-3a LAMBDA 4, 4-DITHIA-6-CHLORO-1,5-DIAZAPENTALENE

BACKGROUND OF THE INVENTION

1. The Invention

This invention relates to certain 2-(N-phenylcarboxamide derivatives) of 3-oxa-3a lambda[4],4-dithia-6-chloro-1,5-diazapentalenes and to method of preparing such compounds. In a further aspect, the invention relates to fungicidal compositions containing such compounds and to the control of certain fungi via the application of such compounds and compositions.

2. The Prior Art

The following publications disclose azapentalenes and thiapentalenes of a variety of structures: (1) D. H. Reid et al, JCS 775 (1975); (2) R. M. Christie et al, JCS 848 (1977); (3) C. Th. Pedersen, JCS 994 (1977); (4) D. H. Reid et al, JCS 2097 (1975); (5) R. H. Reid et al, JCS 854 (1977) and (6) G. L'Abbe et al, Angew. Chem. Int. Ed. Engl. 16 (1977) No. 6.

U.S. Pat. No. 4,059,590 discloses a process for preparing fungicidal 4-halo-5-aryl-1,2,3-dithiazole which comprises reacting an N-arylthioformamide with a sulfur halide in the presence of an ammonium salt. In my prior application Ser. No. 866,122 filed, Dec. 30, 1977, now U.S. Pat. No. 4,179,441 I disclosed certain 2-substituted-3-oxa-3a lambda[4]-4-dithia-6-halo-1,5-diazapentalenes having fungicidal and herbicidal activity.

SUMMARY OF THE INVENTION

I have now discovered a new group of 2-substituted oxadithiadiazapentalene compounds having very good preventative fungicidal and also some eliminative (or direct) activity against certain types of fungi (e.g., tomato late blight, and grape downy mildew, etc.) and virtually no herbicidal activity. Thus, the compounds can be safely applied to vegetation to control certain species of fungi.

The compounds of the invention can be represented by the following formula:

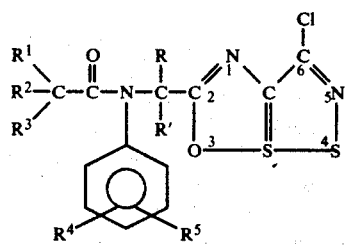

wherein

R, and R' are independently selected from the group of hydrogen and lower alkyl;

$R^1$ is hydrogen or lower alkyl;

$R^2$ and $R^3$ are independently selected from the group of hydrogen, lower alkenyl, hydroxy, lower hydroxyalkyl, lower alkoxy, lower alkoxyalkyl, lower alkoxyalkenyl, lower alkylthio, halogen or haloalkyl having 1 through 3 carbon atoms and from 1 through 4 halo atoms; or $R^2$ and $R^3$ together are lower alkylidiene or lower alkoxyalkylidiene; or $R^2$ and $R^3$ together with the carbon atom to which they are joined form a cycloalkyl group having from 3 through 7 carbon atoms; and $R^4$ and $R^5$ are independently selected from the group of hydrogen, lower alkyl, lower alkoxy, halogen, haloalkyl having from 1 to 2 carbon atoms and 1 to 3 halo atoms, nitro, cyano, and di(lower alkyl)amino; and compatible addition salts (for example wherein $R^4$ and/or $R^5$ is alkylamino) are also encompassed within the invention.

In another embodiment the invention comprises a fungicidal composition comprising a fungicidally effective amount of the above compound(s) and a compatible carrier.

In still another embodiment, the invention comprises controlling fungi via the application of the above compounds and/or composition to fungi or environments susceptible to fungi.

FURTHER DESCRIPTION OF THE INVENTION AND PREFERRED EMBODIMENTS

Considering now the invention in greater detail, typical illustrations of the compounds of the invention can be had by reference to Examples 1 and 2 set forth on pages 18–30 hereinbelow. The preferred compounds in terms of fungicidal properties and/or plant compatibility (expressed in terms of substituent classes) are those wherein R is methyl or ethyl. Preferably R' is hydrogen or methyl. Preferably $R^1$ is hydrogn, methyl, or ethyl. Preferably one of $R^2$ or $R^3$ is hydrogen or methyl. More preferably one of $R^2$ or $R^3$ is hydrogen or methyl and the other is chloro, methoxy, or ethoxy. Preferably $R^4$ is chloro or trifluoromethyl. Preferably $R^5$ is chloro or trifluoromethyl.

Another preferred group of compounds are those wherein one of R or R' is hydrogen and the other hydrogen, methyl or ethyl, $R^1$ is hydrogen; $R^2$ is hydrogen or chloro; $R^3$ is chloro, methoxy or ethoxy; and $R^4$ is hydrogen, chloro, trifluoromethyl, methyl, or ethyl and $R^5$ is chloro, trifluoromethyl, methyl or ethyl.

Compounds having a combination of preferred substituents are particularly preferred. The especially preferred preventative fungicides of the invention are:

2-[1-(alpha-chloro-N-3,4-dichlorophenylacetamido)ethyl]-3-oxa-3a lambda[4],4-dithia-6-chloro-1,5-diazapentalene;

2-[1-(alpha-methoxy-N-3,4-dichlorophenylacetamido)ethyl]-3-oxa-3a lambda[4],4-dithia-6-chloro-1,5-diazapentalene;

2-[1-(N-3,4-dichlorophenylcyclopropylformamido)ethyl]-3-oxa-3a lambda[4],4-dithia-6-chloro-1,5-diazapentalene;

2-[1-(N-3,4-dichlorophenylacryloamido)ethyl]-3-oxa-3a lambda[4],4-dithia-6-chloro-1,5-diazapentalene;

2-[1-(N-3,4-dichlorophenylcrotonoamido)ethyl]-3-oxa-3a lambda[4],4-dithia-6-chloro-1,5-diazapentalene;

2-[1-(N-3,4-dichlorophenyl-3-butenoamido)ethyl]-3-oxa-3a lambda[4],4-dithia-6-chloro-1,5-diazapentalene;

2-[1-(alpha-hydroxy-N-3,4-dichlorophenylacetamido)ethyl]-3-oxa-3a lambda[4],4-dithia-6-chloro-1,5-diazapentalene;

2-[1-(beta-methoxy-N-3,4-dichlorophenylpropionamido)ethyl]-3-oxa-3a lambda[4],4-dithia-6-chloro-1,5-diazapentalene;

2-[1-(beta-methoxy-N-3,4-dichlorophenylcrotonoamido)ethyl]-3-oxa-3a lambda[4],4-dithia-6-chloro-1,5-diazapentalene;

2-[1-(alpha-chloro-N-2,6-dimethylphenylacetamido)ethyl]-3-oxa-3a lambda[4],4-dithia-6-chloro-1,5-diazapentalene;

2-[1-(alpha-methoxy-N-2,6-dimethyl-
    phenylacetamido)ethyl]-3-oxa-3a lambda$^4$,4-dithia-6-
    chloro-1,5-diazapentalene;
2-[1-(alpha-chloro-N-3-trifluoromethyl-
    phenylacetamido)ethyl]-3-oxa-3a lambda$^4$,4-dithia-6-
    chloro-1,5-diazapentalene;
2-[1-(alpha-methoxy-N-3-trifluoromethyl-
    phenylacetamido)ethyl]-3-oxa-3a lambda$^4$,4-dithia-6-
    chloro-1,5-diazapentalene;
2-[1-(alpha-methoxy-N-3,4-dichlorophenylacetamido)-
    propyl]-3-oxa-3a lambda$^4$,4-dithia-6-chloro-1,5-
    diazapentalene; and
2-[1-(alpha-ethoxy-N-3,4-dichlorophenylacetamido)e-
    thyl]-3-oxa-3a lambda$^4$,4-dithia-6-chloro-1,5-
    diazapentalene.

Additional examples of preferred compounds are set forth in Table A of Example 3 hereinbelow.

Where the side chain has an asymmetric carbon atom (for example where R is methyl and R' is hydrogen) the compounds exist as optical isomers and correspondingly the respective isomers as well as mixtures thereof are encompassed within Formula I and within the invention. Similarly, where the side chain has a double bond, geometric isomers exist and both the individual isomers and mixtures thereof are encompassed with Formula I and the invention.

DEFINITIONS

As used herein the following terms have the following meanings, unless expressly stated to the contrary.

The term "alkyl" refers to both straight- and branched-chain alkyl groups. Generally, such alkyl groups contain from 1 through 12 carbon atoms. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl and the like.

The term "alkenyl" refers to unsaturated alkyl groups having a double bond (e.g., $CH_3CH=CH(CH_2)_2-$,) and includes both straight- and branched-chain alkenyl groups.

"Lower alkenyl" groups refer to alkenyl groups having from 2 through 6 carbon atoms. Typical lower alkenyl groups include, for example, ethylenyl; but-3-enyl; hex-4-enyl; 2-methylpent-4-enyl and the like.

The term "halo or halogen atom" refers to the groups fluoro, chloro, bromo and iodo.

The term "alkoxy" refers to the group $R^9O-$ wherein $R^9$ is alkyl.

The term "lower alkoxy" refers to alkoxy groups having from 1 through 6 carbon atoms and includes, for example, methoxy, ethoxy, t-butoxy, hexoxy and the like.

The term "lower alkoxyalkyl" refers to groups having the formula $R^9OR^{9'}-$, wherein $R^9$ and $R^{9'}$ are independently lower alkyl. Typical lower alkoxy lower alkyl groups include, for example, methoxymethyl, methoxypropyl, isopropoxybutyl, hexoxyhexyl and the like.

The term "lower alkoxyalkenyl" refers to the group $R^9OR^{10}-$ wherein $R^9$ is lower alkyl and $R^{10}$ is lower alkenyl. Typical lower methoxy lower alkenyl groups include, for example, methoxyethylenyl, E-butoxybut-2-enyl, pentoxy-hex-5-enyl, and the like.

The term "lower alkylidenyl" refers to groups having the formula $R^9=$ wherein $R^9$ is lower alkyl. Such groups include, for example, methylidenyl ($HC=$); ethylidenyl ($CH_3CH=$); hexylidenyl ($CH_3(C_2)_4CH=$), and the like.

The term "lower alkoxyalkylidenyl" refers to groups having the formula $R^9OR^{9'}=$ wherein $R^9O$ is lower alkoxy and $R^{9'}=$ is lower alkylidenyl. Such groups include, for example, methoxymethylidenyl, butoxypropylidenyl, and the like.

The term "lower hydroxyalkyl" refers to the group $HOR^9$ wherein $R^9$ is lower alkyl. Such groups include, for example, hydroxymethyl; hydroxyethyl, hydroxyhexyl, and the like.

The term "acetamido" refers to the group

The term "propionamido" refers to the group

The term "lower alkoxyalkylene" refers to groups wherein both the alkoxy groups is a lower alkoxy group and the alkylene group is a lower alkylene group. Typical alkoxyalkylene groups include, for example, methoxymethylene, pentoxyhexylene and the like.

The term "alkylthio" refers to the group having the formula $R^9S-$ wherein $R^9$ is alkyl. Typical alkylthio groups include, for example, methylthio, ethylthio, t-butylthio and the like. The term "lower alkylthio" refers to such alkylthio groups wherein the alkyl group is a lower alkyl.

The term "di(lower alkyl)amino" refers to the group having the formula

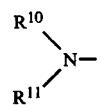

wherein $R^{10}$ and $R^{11}$ are independently selected from the group of alkyl having 1 through 6 carbon atoms. Such groups include, for example, dimethylamino, diethylamino, N-methyl-N-hexylamino, and the like.

The term "haloalkyl" refers to alkyl groups having one or more halo substituents. Typical halo groups include, for example, trifluoromethyl, dichloromethyl, bromochloromethyl, 1,2-dibromoethyl, 3-iodopropyl, 2,2-difluoro-2',2'-diiodoisopropyl and the like.

The term "compatible salt" refers to salts which do not significantly adversely alter the biological and physical properties of the parent compound. Similarly, the term "compatible" carrier refers to carriers which do not significantly adversely alter (save to dilute) the biological and physical properties of the active compound(s).

Synthesis

The compounds of the present invention can be prepared by the following process which can be conveniently represented by the following overall schematic reaction equation:

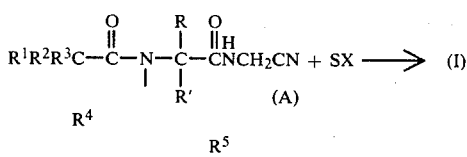

wherein R, R', $R^1$, $R^2$, $R^3$, $R^4$, $R^5$, are as defined hereinabove and SX is sulfur monochloride ($S_2Cl_2$) or sulfur dichloride ($SCl_2$).

This process can be conveniently effected by contacting the appropriate starting material Formula A, having the desired R, R', $R^1$, $R^2$, $R^3$, $R^4$, and $R^5$ substituents with a sulfur chloride (SX), preferably in an inert organic solvent and preferably in the presence of a catalytic amount of a quaternary ammonium salt or an organic nitrogen containing catalyst. The process is typically conducted at temperatures in the range of about from 0 to reflux and preferably about from 0° to 100° C., for about from ½ to 72 hours and preferably about from 24 to 48 hours. Conveniently, the reactants are contacted at about room temperature (about 20°–25° C.) or lower (about from 0° to 25° C.) and the reaction completed at higher temperatures (generally about 25° to 40° C.) Typically a mol ratio of sulfur chloride to the compound of Formula A in the range of about from 2 to 8 mols of sulfur chloride ($S_2Cl_2$ or $SCl_2$) per mol of compound of Formula A and preferably about from 2 to 5 mols of sulfur chloride per mol of compound of Formula A is used. Best results are typically obtained by conducting the process at temperatures in the range of about from 35° to 40° C. for about 24 to 48 hours using about a 1:4 mol ratio of compound of Formula A to sulfur chloride ($S_2Cl_2$ or $SCl_2$).

Where the process is conducted in the presence of a quaternary ammonium salt or an organic nitrogen containing catalyst generally from about 0.01 to 0.3 mol of catalyst per mol of sulfur chloride ($S_2Cl_2$ basis) and preferably about from 0.01 to 0.2 mols per mol of sulfur chloride are used. Suitable quaternary ammonium salts which can be used include, for example, tetralkylammonium halides wherein the alkyl has 1 to 6 carbon atoms and the halide is fluoro, chloro, bromo or iodo, for example, tetraalkylammonium chloride (e.g., tetramethylammonium chloride, tetrabutylammonium chloride) and the like. When a quaternary salt is employed as a catalyst, the anion is preferably a chloride. The term organic nitrogen containing catalyst refers to the group of nitrogen heterocycles; amides; and ureas and includes, for example, di(lower alkyl)aminopyridines, pyridine, dimethylforamide; methylformamide; 1,3-di(-lower alkyl)ureas, and the like. I have found that very good results can be obtained using 4-dimethylaminopyridine or tetrabutylammonium chloride as the catalyst.

Suitable inert organic solvents which can be used, include, for example, alkanes and haloalkanes, such as hexane, isooctane, or dichloromethane; aromatic compounds, such as benzene, toluene, chlorobenzene; oxygenated hydrocarbon such as acyclic alkyl ethers, such as dimethoxyethane and dibutyl ether; and cyclic ethers such as dioxane, tetrahydrofuran, tetrahydropyran and the like and compatible mixtures thereof. Generally, the solvent is employed in amounts of about from 1 to 50 mols per mol of sulfur halide.

The compounds of Formula I can be recovered by any suitable procedure such as, for example, recrystallization; column chromatography; high pressure liquid chromatography. Suitable separation and purification procedures are, for example, described in the appropriate Examples set forth hereinbelow.

The starting materials of Formula A can be prepared by known procedures or by obvious modifications thereof (e.g., substitution of appropriate substrates and solvents). For example, the compounds of Formula A are conveniently prepared by reacting an acid chloride ZCOCl wherein Z corresponds to the desired 2-position side chain of Formula I with a cyanomethylamine.

Also, if desired, where the compound of Formula I has an $R^4$ and/or $R^5$ amino substituent, the acid addition salts of the compounds of Formula I can be prepared by carefully neutralizing the amino moiety of the compound with the appropriate acid. Other addition salts can then be made from this salt by ion exchange with a suitable ion exchange resin having the desired anionic form. Also, if desired, where the compounds exist as optical isomers, the respective optical isomers can be obtained by conventional resolution procedures, for example, by reacting the isomer mixture with an optically active acid which will yield a mixture of optical salts, of the desired compound, which can be resolved by conventional procedures (e.g., crystallization) into the respective plus and minus optical salts.

It should also be appreciated that where typical or preferred process conditions (e.g., reaction temperatures, times, mol ratios of reactants, solvents, etc.) have been given, that other process conditions could also be used, though typically with poorer yields or economies.

Utility

The compounds of the invention exhibit substantial fungicidal activity, and especially preventative fungicidal activity, against a variety of fungi, including tomato leaf blight, celery leaf blight, tomato early blight and grape downy mildew. The compounds further importantly exhibit little, if any, herbicidal activity and thus can be safely applied to vegetation. The compounds can be applied to such fungi but more effectively are applied prophylactically to hosts which are subject to attack from such fungi. The compounds can also be applied to control fungus in domestic and industrial environments. The optimum dosage will, of course, vary with the particular fungi, host, and environment, but typically will be in the range of about from 100 to 1000 ppm by weight based on the weight of active ingredient to solvent. Although the compounds could be applied directly, the fungicides of the invention, as with most pesticidal compounds, are not usually applied full strength, but rather are generally incorporated with conventional biologically inert extenders or carriers normally employed for facilitating dispersion of active fungicidal compounds, recognizing that the formulation and mode of application may affect the activity of the fungicide. Thus, the fungicides of the invention can be formulated and applied as granules, as powdery dusts, as wettable powders, as emulsifiable concentrates, as solutions. or as any of several other known types of formulations, depending on the desired mode of application. Generally the fungicide formulation contains the compounds of the invention in amounts ranging about from 0.005 to 95% by weight and more generally from 1 to 50% by weight. The concentrations will also vary depending upon whether the formulation is intended to be applied directly or further diluted prior to application.

Wettable powders can be in the form of finely divided particles which disperse readily in water or other dispersant. These compositions normally contain from about 5–80% fungicide, and the rest inert material, which includes dispersing agents, emulsifying agents and wetting agents. The powder can be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. Suitable techniques for formulating and applying fungicides are well known in the art.

The fungicidal formulations can also contain stabilizers, spreading agents, sticking agents, fillers, other compatible fungicides and pesticides, and the like.

A further understanding of the invention can be had in the following non-limiting Examples. Wherein, unless expressly stated to the contrary, all temperatures and temperature ranges refer to the Centrigrade system and the term "ambient" or "room temperature" refers to about 20° C.–25° C. The term "percent" or "%" refers to weight percent and the term "mol" or "mols" refers to gram mols. The term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly isomer mixtures are obtained as products. Where given proton-magnetic resonance spectra (p.m.r.) are determined at 60 mHz, and signals are assigned as singlets (s), broad singlets (bs), doublets (d), double doublets (dd), triplets (t), double triplets (dt), quartets (q) and multiplets (m). The abbreviation E.A. refers to elemental analysis.

PREPARATION A

2-Chloro-N-Cyanomethylpropionamide

In this preparation 42 g of 2-chloropropionyl chloride and 27.8 g aminoacetonitrile hydrochloride were admixed with 100 ml of trichloroethylene and stirred at reflux for 5 hours. The reaction mixture was then filtered and the filtrate was distilled to remove the solvent affording 42.6 g of an oily 2-chloro-N-cyanomethylpropionamide product.

PREPARATION B

In this preparation a mixture containing 35.5 g of 2-chloro-N-cyanomethylpropionamide, 30 g of 3,4-dichloroaniline, and 19.7 g. of anhydrous sodium carbonate in 200 ml of dimethyl formamide was stirred at 80°–85° C. for 24 hours. 500 ml of ice water was then added and the resulting mixture was extracted with four 50 ml portions of benzene. The benzene extracts were combined, washed with water, and dried over anhydrous magnesium sulfate and then evaporated affording 45 g of a dark oil. The oil was then applied to a column of 600 g of silica gel and eluted with chloroform and then 5% (volume) methanol:chloroform affording 20 g of a dark oil which partially solidified upon standing. The oil was the dissolved in benzene passed over charcoal and then crystallized affording 18.9 g of 2-(3,4-dichlorophenylamino)-N-cyanomethylpropionamide as a white solid-m.p. 134°–135° C.

Similarly, by following the same procedure but respectively replacing 3,4-dichloroaniline with the corresponding aniline or aniline derivative, the following compounds are respectively prepared:

2-(4-chlorophenylamino)-N-cyanomethylpropionamide;
2-(2-fluorophenylamino)-N-cyanomethylpropionamide;
2-(3-bromophenylamino)-N-cyanomethylpropionamide;
2-(4-iodophenylamino)-N-cyanomethylpropionamide;
2-(3-methylphenylamino)-N-cyanomethylpropionamide;
2-(2-hexylphenylamino)-N-cyanomethylpropionamide;
2-(4-methoxyphenylamino)-N-cyanomethylpropionamide;
2-(3-trifluoromethylphenylamino-N-cyanomethylpropionamide;
2-[2-(1-bromo-2,2-dichloroethyl)phenylamino]-N-cyanomethylpropionamide;
2-(3-nitrophenylamino)-N-cyanomethylpropionamide;
2-(4-cyanophenylamino)-N-cyanomethylpropionamide;
2-(2-dimethylaminophenylamino)-N-cyanomethylpropionamide;
2-phenylamino-N-cyanomethylpropionamide;
2-(3,5-dichlorophenylamino)-N-cyanomethylpropionamide;

2-(3,4-difluorophenylamino)-N-cyanomethylpropionamide;
2-(2,4-difluorophenylamino)-N-cyanomethylpropionamide;
2-(3,4-dibromophenylamino)-N-cyanomethylpropionamide;
2-(3,4-diiodophenylamino)-N-cyanomethylpropionamide;
2-(2,6-dimethylphenylamino)-N-cyanomethylpropionamide;
2-(2,6-diethylphenylamino)-N-cyanomethylpropionamide;
2-(2-methyl-3-t-butylphenylamino)-N-cyanomethylpropionamide;
2-(3,4-dimethoxyphenylamino)-N-cyanomethylpropionamide;
2-(3,4-ditrifluoromethylphenylamino)-N-cyanomethylpropionamide;
2-[2,4-di(1-bromo-2-iodoethyl)phenylamino]-N-cyanomethylpropionamide;
2-(3,4-dinitrophenylamino)-N-cyanomethylpropionamide;
2-(3,4-dicyanophenylamino)-N-cyanomethylpropionamide;
2-[3,4-di(dimethylamino)phenylamino]-N-cyanomethylpropionamide;
2-(3-chloro-4-fluorophenylamino)-N-cyanomethylpropionamide;
2-(3-methyl-4-chlorophenylamino)-N-cyanomethylpropionamide;
2-(2-fluoro-4-t-butylphenylamino)-N-cyanomethylpropionamide;
2-(3-chloro-4-methoxyphenylamino)-N-cyanomethylpropionamide;
2-(3-chloro-4-trifluoromethylphenylamino)-N-cyanomethylpropionamide;
2-(2-cyano-3-chlorophenylamino)-N-cyanomethylpropionamide;
2-(3-nitro-4-trifluoromethylphenylamino)-N-cyanomethylpropionamide;
2-(2-nitro-4-dimethylaminophenylamino)-N-cyanomethylpropionamide;
2-(3-cyano-4-methoxyphenylamino)-N-cyanomethylpropionamide;
2-(3-methyl-4-methoxyphenylamino)-N-cyanomethylpropionamide; and
2-(2-methyl-3-dimethylaminophenyl)-N-cyanopropionamide.

Similarly, by respectively replacing 2-chloro-N-cyanomethylpropionamide with 2-chloro-N-cyanomethylacetamide and 2-chloro-N-cyanomethylbutyramide, the corresponding des-methyl (i.e., acetamide) and ethyl (i.e., butyramide) homologues of each of the above compounds are respectively prepared.

PREPARATION C

This preparation illustrates the preparation of the compounds of Formula A.

In this preparation 25 ml of methylene chloride containing 2.0 g of chloroacetyl chloride were slowly added dropwise over a period of 40 minutes to a stirred mixture containing 15.5 g of 2-(3,4-dichlorophenylamino)-N-cyanomethylpropionamide and 5.4 g of pyridine in 150 ml of methylene chloride at room temperature. After one hour an additional 3.5 g of chloroacetyl chloride (in 25 ml of methylene chloride) and 2.4 g of pyridine were added dropwise as before. The resulting mixture was then refluxed for 20 minutes and then cooled, washed with three 50 ml portions of water, dried over magnesium sulfate and then evaporated affording an oil. The oil was applied to a column of 150 g of silica gel and eluted with 5% (volume) methanol in chloroform mixture affording an oil. The oil was then taken up in 50 ml of hot benzene. 50 ml of hexane was then added and the mixture cooled yielding 3 g of a solid having a melting point of 143°–145° C. One gram of this solid was then recrystallized from benzene-hexane affording 2-(N-chloroacetyl-N-3,4-dichlorophenylamino)-N-cyanomethylpropionamide as a white solid; m.p. 146°–147° C.

Similarly, by following the same procedure, respectively, using the compounds of Preparation B as starting materials, the corresponding N-amino chloroacetyl derivatives of those compounds are respectively prepared.

PREPARATION D

Similarly, by following the same procedure as used in Preparation C above, but respectively replacing chloroacetyl chloride with fluoroacetyl chloride; bromoacetyl chloride; iodoacetyl chloride; methylthioacetyl chloride; trifluoromethylacetyl chloride; difluoroacetyl chloride; dichloroacetyl chloride, bromochloroacetyl chloride; fluoroiodoacetyl chloride; methoxyacetyl chloride; ethoxyacetyl chloride; t-butoxyacetyl chloride; methoxyfluoroacetyl chloride; alpha-chloropropionyl chloride; alpha-methoxy-alpha-fluoropropionyl chloride; and alpha-bromovaleryl chloride, the corresponding N'-fluoroacetyl; N'-bromoacetyl, N'-iodoacetyl, N'-methylthioacetyl; N'-trifluoromethylacetyl; N'-difluoroacetyl; N'-dichloroacetyl; N'-bromochloroacetyl; N'-fluoroiodoacetyl, N'-methoxyacetyl; N'-t-butoxyacetyl; N'-methoxyfluoroacetyl, N'-alpha-chloropropionyl; N'-alpha-methoxy-alpha-fluoropropionyl and N'-alpha-bromovaleryl analogs of each of the above compounds is respectively prepared, for example:

2-(N-bromoacetyl-N-3,4-dichlorophenylamino)-N-cyanomethylpropionamide;
2-(N-iodoacetyl-N-3,4-dichlorophenylamino)-N-cyanomethylpropionamide;
2-(N-methylthioacetyl-N-3,4-dichlorophenylamino)-N-cyanomethylpropionamide;
2-(N-trifluoromethylacetyl-N-3,4-dichlorophenylamino)-N-cyanomethylpropionamide;
2-(N-difluoroacetyl-N-3,4-dichlorophenylamino)-N-cyanomethylpropionamide;
2-(N-dichloroacetyl-N-3,4-dichlorophenylamino)-N-cyanomethylpropionamide;
2-(N-bromochloroacetyl-N-3,4-dichlorophenylamino)-N-cyanomethylpropionamide;
2-(N-fluoroiodoacetyl-N-3,4-dichlorophenylamino)-N-cyanomethylpropionamide;
2-(N-methoxyacetyl-N-3,4-dichlorophenylamino)-N-cyanomethylpropionamide;
2-(N-methoxyacetyl-N-2,6-dimethylphenylamino)-N-cyanomethylpropionamide;
2-(N-methoxyacetyl-N-2,6-diethylphenylamino)-N-cyanomethylpropionamide;
2-(N-methoxyacetyl-N-2-methyl-6-ethylphenylamino)-N-cyanomethylpropionamide;
2-(N-methoxyacetyl-N-3-trifluoromethylphenylamino)-N-cyanomethylpropionamide;
2-(N-methoxyacetyl-N-3,5-dichlorophenylamino)-N-cyanomethylpropionamide;

2-(N-methoxyacetyl-N-4-chlorophenylamino)-N-cyanomethylpropionamide;
2-(N-methoxyacetyl-N-3,4-dichlorophenylamino)-N-cyanomethylacetamide;
2-(N-methoxyacetyl-N-3,4-dichlorophenylamino)-N-cyanomethylbutyramide;
2-(N-ethoxyacetyl-N-3,4-dichlorophenylamino)-N-cyanomethylpropionamide;
2-(N-t-butoxyacetyl-N-3,4-dichlorophenylamino)-N-cyanomethylpropionamide;
2-(N-methoxyfluoroacetyl-N-3,4-dichlorophenylamino)-N-cyanomethylpropionamide;
2-(N-alpha-chloropropionyl-N-3,4-dichlorophenylamino)-N-cyanomethylpropionamide;
2-(N-alpha-methoxy-alpha-fluoropropionyl-N-3,4-dichlorophenylamino)-N-cyanomethylpropionamide;
2-(N-alpha-bromovaleryl-N-3,4-dichlorophenylamino)-N-cyanomethylpropionamide, etc.

PREPARATION E

Similarly, by following the same procedure as used in Preparation C above, but respectively replacing chloroacetyl chloride with acryloyl chloride; crotonoylacetyl chloride; but-3-enoyl chloride; beta-methoxycrotonoyl chloride; beta-methoxypropionyl chloride; and cyclopropylformyl chloride; the corresponding N'-acryloyl; N'-crotonoyl; N'-but-3-enoyl; N'-beta-methoxycrotonoyl; N'-beta-methoxypropionyl; and N'-cyclopropylformyl analogs of each of the above compounds is respectively prepared, for example:
2-(N-acryloyl-N-3,4-dichlorophenylamino)-N-cyanomethylpropionamide;
2-(N-crotonoyl-N-3,4-dichlorophenylamino)-N-cyanomethylpropionamide;
2-(N-but-3-enoyl-N-3,4-dichlorophenylamino)-N-cyanomethylpropionamide;
2-(N-beta-methoxycrotonoyl-N-3,4-dichlorophenylamino)-N-cyanomethylpropionamide;
2-(N-beta-methoxypropionyl-N-3,4-dichlorophenylamino)-N-cyanomethylpropionamide;
2-(N-cyclopropylformyl-N-3,4-dichlorophenylamino)-N-cyanomethylpropionamide; etc.

EXAMPLE 1

This example illustrates the preparation of the compounds of Formula I.

In this example 7.3 g of 2-(N-chloroacetyl-N-3,4-dichlorophenylamino)-N-cyanomethylpropionamide, 0.5 g of tetrabutylammonium chloride, 11.3 g sulfur monochloride ($S_2Cl_2$) and 150 ml of methylene dichloride were stirred together at room temperature resulting in a lemon yellow solution which darkened to cherry red after about four hours. The mixture was then stirred for another 16 hours during which time a solid product precipitated out. The mixture was then filtered and the resulting filter cake was dried and then stirred with 75 ml of toluene and refluxed for ten minutes affording a clear solution. The toluene was then removed by evaporation affording an oil which slowly solidified upon standing. The solid was then crystallized from a mixture of benzene and hexane affording 2-[1-(alpha-chloro-N-3,4-dichlorophenyl-acetamide)ethyl]-3-oxa-3a lambda$^4$,4-dithia-6-chloro-1,5-diazapentalene, m.p. 143°-144° C.

Similarly, by following the same procedure using the corresponding compounds of formula A as starting material, the following compounds are respectively prepared:

2-[1-(alpha-chloro-N-4-chlorophenylacetamido)ethyl]-3-oxa-3a lambda$^4$,4-dithia-6-chloro-1,5-diazapentalene, 125°-127° C.;
2-[1-(alpha-chloro-N-2-fluorophenylacetamido)ethyl]-3-oxa-3a lambda$^4$,4-dithia-6-chloro-1,5-diazapentalene;
2-[1-(alpha-chloro-N-3-bromophenylacetamido)ethyl]-3-oxa-3a lambda$^4$,4-dithia-6-chloro-1,5-diazapentalene;
2-[1-(alpha-chloro-N-4-iodophenylacetamido)ethyl]-3-oxa-3a lambda$^4$,4-dithia-6-chloro-1,5-diazapentalene;
2-[1-alpha-chloro-N-3-methylphenylacetamido)ethyl]-3-oxa-3a lambda$^4$,4-dithia-6-chloro-1,5-diazapentalene;
2-[1-(alpha-chloro-N-2-hexylphenylacetamido)ethyl]-3-oxa-3a lambda$^4$,4-dithia-6-chloro-1,5-diazapentalene;
2-[1-(alpha-chloro-N-4-methoxyphenylacetamido)ethyl]-3-oxa-3a lambda$^4$,4-dithia-6-chloro-1,5-diazapentalene;
2-[1-(alpha-chloro-N-3-trifluoromethylphenylacetamido)ethyl]-3-oxa-3a lambda$^4$,4-dithia-6-chloro-1,5-diazapentalene, m.p. glass, E.A. calc % C-37.86, H-2.27, N-9.45, found % C-36.13, H-2.17, N-8.58;
2-[1-(alpha-chloro-N-2-[1-bromo-2,2-dichloroethyl]-phenylacetamido)ethyl]-3-oxa-3a lambda$^4$,4-dithia-6-chloro-1,5-diazapentalene;
2-[1-(alpha-chloro-N-3-nitrophenylacetamido)ethyl]-3-oxa-3a lambda$^4$,4-dithia-6-chloro-1,5-diazapentalene;
2-[1-(alpha-chloro-N-4-cyanophenylacetamido)ethyl]-3-oxa-3a lambda$^4$,4-dithia-6-chloro-1,5-diazapentalene;
2-[1-(alpha-chloro-N-2-dimethylaminophenylacetamido)ethyl]-3-oxa-3a lambda$^4$,4-dithia-6-chloro-1,5-diazapentalene;
2-[1-(alpha-chloro-N-phenylacetamido)ethyl]-3-oxa-3a lambda$^4$,4-dithia-6-chloro-1,5-diazapentalene;
2-[1-(alpha-chloro-N-3,5-dichlorophenylacetamido)ethyl]-3-oxa-3a lambda$^4$,4-dithia-6-chloro-1,5-diazapentalene, m.p. 162°-163° C.;
2-[1-(alpha-chloro-N-3,4-difluorophenylacetamido)ethyl]-3-oxa-3a lambda$^4$,4-dithia-6-chloro-1,5-diazapentalene;
2-[1-(alpha-chloro-N-2,4-difluorophenylacetamido)ethyl]-3-oxa-3a lambda$^4$,4-dithia-6-chloro-1,5-diazapentalene;
2-[1-(alpha-chloro-N-3,4-dibromophenylacetamido)ethyl]-3-oxa-3a lambda$^4$,4-dithia-6-chloro-1,5-diazapentalene;
2-[1-(alpha-chloro-N-3,4-diiodophenylacetamido)ethyl]-3-oxa-3a lambda$^4$,4-dithia-6-chloro-1,5-diazapentalene;
2-[1-(alpha-chloro-N-2,6-dimethylphenylacetamido)ethyl]-3-oxa-3a lambda$^4$,4-dithia-6-chloro-1,5-diazapentalene, m.p. 138°-139° C.;
2-[1-(alpha-chloro-N-2,6-diethylphenylacetamido)ethyl]-3-oxa-3a lambda$^4$,4-dithia-6-chloro-1,5-diazapentalene, m.p. glass, E.A. calc % C-47.22, H-4.44, N-9.71 found % C-45.12, H-4.20, N-9.19;
2-[1-(alpha-chloro-N-2-methyl-3-t-butylphenylacetamido)ethyl]-3-oxa-3a lambda$^4$,4-dithia-6-chloro-1,5-diazapentalene;
2-[1-(alpha-chloro-N-3,4-dimethoxyphenylacetamido)ethyl]-3-oxa-3a lambda$^4$,4-dithia-6-chloro-1,5-diazapentalene;
2-[1-(alpha-chloro-N-3,4-ditrifluoromethylphenylacetamido)ethyl]-3-oxa-3a lambda$^4$,4-dithia-6-chloro-1,5-diazapentalene;

2-[1-(alpha-chloro-N-2,4-di[1-bromo-2-iodoethyl]-phenylacetamido)ethyl]-3-oxa-3a lambda⁴,4-dithia-6-chloro-1,5-diazapentalene;
2-[1-(alpha-chloro-N-3,4-dinitrophenylacetamido)ethyl]-3-oxa-3a lambda⁴,4-dithia-6-chloro-1,5-diazapentalene;
2-[1-(alpha-chloro-N-3,4-dicyanophenylacetamido)ethyl]-3-oxa-3a lambda⁴,4-dithia-6-chloro-1,5-diazapentalene;
2-[1-(alpha-chloro-N-3,4-di[dimethylamino]-phenylacetamido)ethyl]-3-oxa-3a lambda⁴,4-dithia-6-chloro-1,5-diazapentalene;
2-[1-(alpha-chloro-N-3-chloro-4'-fluoro-phenylacetamido)ethyl]-3-oxa-3a lambda⁴,4-dithia-6-chloro-1,5-diazapentalene;
2-[1-(alpha-chloro-N-3-bromo-4-chloro-phenylacetamido)ethyl]-3-oxa-3a lambda⁴,4-dithia-6-chloro-1,5-diazapentalene;
2-[1-(alpha-chloro-N-3-methyl-4-chloro-phenylacetamido)ethyl]-3-oxa-3a lambda⁴,4-dithia-6-chloro-1,5-diazapentalene;
2-[1-(alpha-chloro-N-2-fluoro-4-t-butyl-phenylacetamido)ethyl]-3-oxa-3a lambda⁴,4-dithia-6-chloro-1,5-diazapentalene;
2-[1-(alpha-chloro-N-3-chloro-4-methoxy-phenylacetamido)ethyl]-3-oxa-3a lambda⁴,4-dithia-6-chloro-1,5-diazapentalene;
2-[1-(alpha-chloro-N-3-chloro-4-trifluoromethyl-phenylacetamido)ethyl]-3-oxa-3a lambda⁴,4-dithia-6-chloro-1,5-diaza-pentalene;
2-[1-(alpha-chloro-N-2-cyano-3-chloro-phenylacetamido)ethyl]-3-oxa-3a lambda⁴,4-dithia-6-chloro-1,5-diazapentalene;
2-[1-(alpha-chloro-N-3-nitro-4-trifluoromethyl-phenylacetamido)ethyl]-3-oxa-3a lambda⁴,4-dithia-6-chloro-1,5-diaza-pentalene;
2-[1-(alpha-chloro-N-2-nitro-4-dimethylamino-phenylacetamido)ethyl]-3-oxa-3a lambda⁴,4-dithia-6-chloro-1,5-diaza-pentalene;
2-[1-(alpha-chloro-N-3-cyano-4-methoxy-phenylacetamido)ethyl]-3-oxa-3a lambda⁴,4-dithia-6-chloro-1,5-diazapentalene;
2-[1-(alpha-chloro-N-3-methyl-4-methoxy-phenylacetamido)ethyl]-3-oxa-3a lambda⁴,4-dithia-6-chloro-1,5-diazapentalene;
2-[1-(alpha-chloro-N-2-methyl-4-dimethylamino-phenylacetamido)ethyl]-3-oxa-3a lambda⁴,4-dithia-6-chloro-1,5-diazapentalene;
2-[(alpha-chloro-N-3,4-dichlorophenylacetamido)methyl]-3-oxa-3a lambda⁴,4-dithia-6-chloro-1,5-diazapentalene;
2-[(alpha-chloro-N-4-chlorophenylacetamido)methyl]-3-oxa-3a lambda⁴,4-dithia-6-chloro-1,5-diazapentalene;
2-[(alpha-chloro-N-2-fluorophenylacetamido)methyl]-3-oxa-3a lambda⁴,4-dithia-6-chloro-1,5-diazapentalene;
2-[(alpha-chloro-N-3-bromophenylacetamido)methyl]-3-oxa-3a lambda⁴,4-dithia-6-chloro-1,5-diazapentalene;
2-[(alpha-chloro-N-4-iodophenylacetamido)methyl]-3-oxa-3a lambda⁴,4-dithia-6-chloro-1,5-diazapentalene;
2-[(alpha-chloro-N-3-methylphenylacetamido)methyl]-3-oxa-3a lambda⁴,4-dithia-6-chloro-1,5-diazapentalene;
2-[(alpha-chloro-N-2-hexylphenylacetamido)methyl]-3-oxa-3a lambda⁴,4-dithia-6-chloro-1,5-diazapentalene;
2-[(alpha-chloro-N-4-methoxyphenylacetamido)methyl]-3-oxa-3a lambda⁴,4-dithia-6-chloro-1,5-diazapentalene;
2-[(alpha-chloro-N-4-trifluoromethyl-phenylacetamido)methyl]-3-oxa-3a lambda⁴,4-dithia-6-chloro-1,5-diazapentalene;
2-[(alpha-chloro-N-2-[1-bromo-2,2-dichloroethyl]-phenylacetamido)methyl]-3-oxa-3a lambda⁴,4-dithia-6-chloro-1,5-diazapentalene;
2-[(alpha-chloro-N-3-nitrophenylacetamido)methyl]-3-oxa-3a lambda⁴,4-dithia-6-chloro-1,5-diazapentalene;
2-[(alpha-chloro-N-4-cyanophenylacetamido)methyl]-3-oxa-3a lambda⁴,4-dithia-6-chloro-1,5-diazapentalene;
2-[(alpha-chloro-N-2-dimethylaminophenylacetamido)methyl]-3-oxa-3a lambda⁴,4-dithia-6-chloro-1,5-diazapentalene;
2-[(alpha-chloro-N-phenylacetamido)methyl]-3-oxa-3a lambda⁴,4-dithia-6-chloro-1,5-diazapentalene;
2-[(alpha-chloro-N-2,3-dichlorophenylacetamido)methyl]-3-oxa-3a lambda⁴,4-dithia-6-chloro-1,5-diazapentalene;
2-[(alpha-chloro-N-3,4-difluorophenylacetamido)methyl]-3-oxa-3a lambda⁴,4-dithia-6-chloro-1,5-diazapentalene;
2-[(alpha-chloro-N-2,4-difluorophenylacetamido)methyl]-3-oxa-3a lambda⁴,4-dithia-6-chloro-1,5-diazapentalene;
2-[(alpha-chloro-N-3,4-dibromophenylacetamido)methyl]-3-oxa-3a lambda⁴,4-dithia-6-chloro-1,5-diazapentalene;
2-[(alpha-chloro-N-3,4-diiodophenylacetamido)methyl]-3-oxa-3a lambda⁴,4-dithia-6-chloro-1,5-diazapentalene;
2-[(alpha-chloro-N-3,4-dimethylphenylacetamido)methyl]-3-oxa-3a lambda⁴,4-dithia-6-chloro-1,5-diazapentalene;
2-[(alpha-chloro-N-2-methyl-3-t-butyl-phenylacetamido)methyl]-3-oxa-3a lambda⁴,4-dithia-6-chloro-1,5-diazapentalene;
2-[(alpha-chloro-N-3,4-dimethoxyphenylacetamido)methyl]-3-oxa-3a lambda⁴,4-dithia-6-chloro-1,5-diazapentalene;
2-[(alpha-chloro-N-3,4-ditrifluoromethyl-phenylacetamido)methyl]-3-oxa-3a lambda⁴,4-dithia-6-chloro-1,5-diazapentalene;
2-[(alpha-chloro-N-2,4-di[1-bromo-2-iodoethyl]-phenylacetamido)methyl]-3-oxa-3a lambda⁴,4-dithia-6-chloro-1,5-diazapentalene;
2-[(alpha-chloro-N-3,4-dinitrophenylacetamido)methyl]-3-oxa-3a lambda⁴,4-dithia-6-chloro-1,5-diazapentalene;
2-[(alpha-chloro-N-3,4-dicyanophenylacetamido)methyl]-3-oxa-3a lambda⁴,4-dithia-6-chloro-1,5-diazapentalene;
2-[(alpha-chloro-N-3,4-di[dimethylamino]-phenylacetamido)methyl]-3-oxa-3a lambda⁴,4-dithia-6-chloro-1,5-diazapentalene;
2-[(alpha-chloro-N-[3-chloro-4-fluoro]-phenylacetamido)methyl]-3-oxa-3a lambda⁴,4-dithia-6-chloro-1,5-diazapentalene;
2-[(alpha-chloro-N-3-bromo-4-chloro-phenylacetamido)methyl]-3-oxa-3a lambda⁴,4-dithia-6-chloro-1,5-diazapentalene;
2-[(alpha-chloro-N-3-methyl-4-chloro-phenylacetamido)methyl]-3-oxa-3a lambda⁴,4-dithia-6-chloro-1,5-diazapentalene;

2-[(alpha-chloro-N-2-fluoro-4-t-butyl-phenylacetamido)methyl]-3-oxa-3a lambda$^4$,4-dithia-6-chloro-1,5-diazapentalene;

2-[(alpha-chloro-N-3-chloro-4-methoxy-phenylacetamido)methyl]-3-oxa-3a lambda$^4$,4-dithia-6-chloro-1,5-diazapentalene;

2-[(alpha-chloro-N-3-chloro-4-trifluoromethyl-phenylacetamido)-methyl]-3-oxa-3a lambda$^4$,4-dithia-6-chloro-1,5-diazapentalene;

2-[(alpha-chloro-N-2-cyano-3-chlorophenylacetamido)-methyl]-3-oxa-3a lambda$^4$,4-dithia-6-chloro-1,5-diazapentalene;

2-[(alpha-chloro-N-3-nitro-4-trifluoromethyl-phenylacetamido)methyl]-3-oxa-3a lambda$^4$,4-dithia-6-chloro-1,5-diazapentalene;

2-[(alpha-chloro-N-2-nitro-4-dimethylamino-phenylacetamido)methyl]-3-oxa-3a lambda$^4$,4-dithia-6-chloro-1,5-diazapentalene;

2-[(alpha-chloro-N-3-cyano-4-methoxy-phenylacetamido)methyl]-3-oxa-3a lambda$^4$,4-dithia-6-chloro-1,5-diazapentalene;

2-[(alpha-chloro-N-2-methyl-3-methoxy-phenylacetamido)methyl]-3-oxa-3a lambda$^4$,4-dithia-6-chloro-1,5-diazapentalene;

2-[(alpha-chloro-N-2-methyl-3-dimethylamino-phenylacetamido)methyl]-3-oxa-3a lambda$^4$,4-dithia-6-chloro-1,5-diazapentalene;

2-[2-(alpha-chloro-N-3,4-dichlorophenylacetamido)-butyl]-3-oxa-3a lambda$^4$,4-dithia-6-chloro-1,5-diazapentalene;

2-[2-(alpha-chloro-N-4-chlorophenylacetamido)butyl]-3-oxa-3a lambda$^4$,4-dithia-6-chloro-1,5-diazapentalene;

2-[2-(alpha-chloro-N-2-fluorophenylacetamido)butyl]-3-oxa-3a lambda$^4$,4-dithia-6-chloro-1,5-diazapentalene;

2-[2-(alpha-chloro-N-3-bromophenylacetamido)butyl]-3-oxa-3a lambda$^4$,4-dithia-6-chloro-1,5-diazapentalene;

2-[2-(alpha-chloro-N-4-iodophenylacetamido)butyl]-3-oxa-3a lambda$^4$,4-dithia-6-chloro-1,5-diazapentalene;

2-[(alpha-chloro-N-3-methylphenylacetamido)butyl]-3-oxa-3a lambda$^4$,4-dithia-6-chloro-1,5-diazapentalene;

2-[(alpha-chloro-N-2-hexylphenylacetamido)butyl]-3-oxa-3a lambda$^4$,4-dithia-6-chloro-1,5-diazapentalene;

2-[(alpha-chloro-N-4-methoxyphenylacetamido)-butyl]-3-oxa-3a lambda$^4$,4-dithia-6-chloro-1,5-diazapentalene;

2-[2-(alpha-chloro-N-4-trifluoromethyl-phenylacetamido)butyl]-3-oxa-3a lambda$^4$,4-dithia-6-chloro-1,5-diazapentalene;

2-[2-(alpha-chloro-N-2-[1-bromo-2,2-dichloroethyl]-phenylacetamido)-butyl]-3-oxa-3a lambda$^4$,4-dithia-6-chloro-1,5-diazapentalene;

2-[2-(alpha-chloro-N-3-nitrophenylacetamido)butyl]-3-oxa-3a lambda$^4$,4-dithia-6-chloro-1,5-diazapentalene;

2-[2-(alpha-chloro-N-4-cyanophenylacetamido)butyl]-3-oxa-3a lambda$^4$,4-dithia-6-chloro-1,5-diazapentalene;

2-[2-(alpha-chloro-N-2-dimethylamino-phenylacetamido)butyl]-oxa-3a lambda$^4$,4-dithia-6-chloro-1,5-diazapentalene;

2-[2-(alpha-chloro-N-phenylacetamido)butyl]-3-oxa-3a lambda$^4$,4-dithia-6-chloro-1,5-diazapentalene;

2-2-(alpha-chloro-N-2,3-dichlorophenylacetamido)-butyl]-3-oxa-3a lambda$^4$,4-dithia-6-chloro-1,5-diazapentalene;

2-[2-(alpha-chloro-N-3,4-difluorophenylacetamido)-butyl]-3-oxa-3a lambda$^4$,4-dithia-6-chloro-1,5-diazapentalene;

2-[(alpha-chloro-N-2,4-difluorophenylacetamido)-butyl]-3-oxa-3a lambda$^4$,4-dithia-6-chloro-1,5-diazapentalene;

2-[(alpha-chloro-N-3,4-dibromophenylacetamido)-butyl]-3-oxa-3a lambda$^4$,4-dithia-6-chloro-1,5-diazapentalene;

2-[2-(alpha-chloro-N-3,4-diiodophenylacetamido)-butyl]-3-oxa-3a lambda$^4$,4-dithia-6-chloro-1,5-diazapentalene;

2-[(alpha-chloro-N-3,4-dimethylphenylacetamido)-butyl]-3-oxa-3a lambda$^4$,4-dithia-6-chloro-1,5-diazapentalene;

2-[2-(alpha-chloro-N-2-methyl-3-t-butyl-phenylacetamido)butyl]-3-oxa-3a lambda$^4$,4-dithia-6-chloro-1,5-diazapentalene;

2-[2-(alpha-chloro-N-3,4-dimethoxyphenylacetamido)-butyl]-3-oxa-3a lambda$^4$,4-dithia-6-chloro-1,5-diazapentalene;

2-[b 2-(alpha-chloro-N-3,4-ditrifluoromethyl-phenylacetamido)butyl]-3-oxa-3a lambda$^4$,4-dithia-6-chloro-1,5-diazapentalene;

2-[2-(alpha-chloro-N-2,4-di[1-bromo-2-iodoethyl]-phenylacetamido)butyl]-3-oxa-3a lambda$^4$,4-dithia-6-chloro-1,5-diazapentalene;

2-[2-(alpha-chloro-N-3,4-dinitrophenylacetamido)-butyl]-3-oxa-3a lambda$^4$,4-dithia-6-chloro-1,5-diazapentalene;

2-[2-(alpha-chloro-N-3,4-dicyanophenylacetamido)-butyl]-3-oxa-3a lambda$^4$,4-dithia-6-chloro-1,5-diazapentalene;

2-[2-(alpha-chloro-N-3,4-di[dimethylamino]-phenylacetamido)butyl]-3-oxa-3a lambda$^4$,4-dithia-6-chloro-1,5-diazapentalene;

2-[(alpha-chloro-N-3-chloro-4-fluoro-phenylacetamido)butyl]-3-oxa-3a lambda$^4$,4-dithia-6-chloro-1,5-diazapentalene;

2-[(alpha-chloro-N-3-bromo-4-chloro-phenylacetamido)butyl]-3-oxa-3a lambda$^4$,4-dithia-6-chloro-1,5-diazapentalene;

2-[(alpha-chloro-N-3-methyl-4-chloro-phenylacetamido)butyl]-3-oxa-3a lambda$^4$,4-dithia-6-chloro-1,5-diazapentalene;

2-[2-(alpha-chloro-N-2-fluoro-4-t-butyl-phenylacetamido)butyl]-3-oxa-3a lambda$^4$,4-dithia-6-chloro-1,5-diazapentalene;

2-[(alpha-chloro-N-3-chloro-4-methoxy-phenylacetamido)butyl]-3-oxa-3a lambda$^4$,4-dithia-6-chloro-1,5-diazapentalene;

2-[(alpha-chloro-N-3-chloro-4-trifluoromethyl-phenylacetamido)butyl]-3-oxa-3a lambda$^4$,4-dithia-6-chloro-1,5-diazapentalene;

2-(alpha-chloro-N-2-cyano-3-chloro-phenylacetamido)butyl]-3-oxa-3a lambda$^4$,4-dithia-6-chloro-1,5-diazapentalene;

2-[2-(alpha-chloro-N-3-nitro-4-trifluoromethyl-phenylacetamido)butyl]-3-oxa-3a lambda$^4$,4-dithia-6-chloro-1,5-diazapentalene;

2-[2-(alpha-chloro-N-2-nitro-4-dimethylamino-phenylacetamido)butyl]-3-oxa-3a lambda$^4$,4-dithia-6-chloro-1,5-diazapentalene;

2-[2-(alpha-chloro-N-3-cyano-4-methoxy-phenylacetamido)butyl]-3-oxa-3a lambda$^4$,4-dithia-6-chloro-1,5-diazapentalene;

2-[2-(alpha-chloro-N-2-methyl-3-methoxy-phenylacetamido)butyl]-3-oxa-3a lambda$^4$,4-dithia-6-chloro-1,5-diazapentalene; and 2-[2-(alpha-chloro-N-2-methyl-3-dimethylamino-phenylacetamido)butyl]-3-oxa-3a lambda$^4$,4-dithia-6-chloro-1,5-diazapentalene.

Similarly, by following the same procedure but using the corresponding compounds of Preparation D as starting materials, the corresponding fluoro, bromo, iodo, difluoro; dichloro; bromochloro; fluoroiodo; methoxy; t-butoxy; methoxy-fluoro; chloro-methyl; methoxy-methyl and bromo-butyl acetamido derivatives of each of the above compounds are prepared including, for example:

2-[2-(alpha-fluoro-N-3,4-dichlorophenylacetamido)ethyl]-3-oxa-3a lambda$^4$,4-dithio-6-chloro-1,5-diazapentalene;

2-[2-(alpha-bromo-N-3,4-dichlorophenylacetamido)ethyl]-3-oxa-3a lambda$^4$,4-dithio-6-chloro-1,5-diazapentalene;

2-[2-(alpha-iodo-N-3,4-dichlorophenylacetamido)ethyl]-3-oxa-3a lambda$^4$,4-dithio-6-chloro-1,5-diazapentalene;

2-[2-(alpha-methylthio-N-3,4-dichlorophenylacetamido)ethyl]-3-oxa-3a lambda$^4$,4-dithio-6-chloro-1,5-diazapentalene;

2-[2-(alpha,alpha-difluoro-N-3,4-dichlorophenylacetamido)ethyl]-3-oxa-3a lambda$^4$,4-dithio-6-chloro-1,5-diazapentalene;

2-[2-(alpha,alpha-dichloro-N-3,4-dichlorophenylacetamido)ethyl]-3-oxa-3a lambda$^4$,4-dithio-6-chloro-1,5-diazapentalene, m.p. glass, E.A. calc % C-32.55, H-1.69, N-8.76 found % C-33.76, H-1.89, N-8.82;

2-[2-(alpha-bromo-alpha-chloro-N-3,4-dichlorophenylacetamido)ethyl]-3-oxa-3a lambda$^4$,4-dithio-6-chloro-1,5-diazapentalene;

2-[2-(alpha-fluoro-alpha-iodo-N-3,4-dichlorophenylacetamido)ethyl]-3-oxa-3a lambda$^4$,4-dithio-6-chloro-1,5-diazapentalene;

2-[2-(alpha-methoxy-N-3,4-dichlorophenylacetamido)ethyl]-3-oxa-3a lambda$^4$,4-dithio-6-chloro-1,5-diazapentalene, m.p. 120°-121° C.;

2-[1-(alpha-methoxy-N-2,6-dimethyl-phenylacetamido)ethyl]-3-oxa-3a lambda$^4$,4-dithio-6-chloro-1,5-diazapentalene, m.p. 158°-159° C.;

2-[1-(alpha-methoxy-N-2,6-diethylphenylacetamido)ethyl]-3-oxa-3a lambda$^4$,4-dithio-6-chloro-1,5-diazapentalene, m.p. 120°-123° C.;

2-[1-alpha-methoxy-N-2-methyl-6-ethyl-phenylacetamido)ethyl]-3-oxa-3a lambda$^4$,4-dithio-6-chloro-1,5-diazapentalene m.p. glass, E.A. calc % C-49.34, H-4.88, N-10.5, found % C-49.01, H-4.87, N-10.44;

2-[1-(alpha-methoxy-N-3-trifluoromethyl-phenylacetamido)ethyl]-3-oxa-3a lambda$^4$,4-dithio-6-chloro-1,5-diazapentalene, m.p. glass, E.A. calc % C-40.97, H-2.98, N-9.55, found % C-39.21, H-3.14, N-8.95;

2-[1-(alpha-methoxy-N-3,5-dichlorophenylacetamido)ethyl]-3-oxa-3a lambda$^4$,4-dithio-6-chloro-1,5-diazapentalene, m.p. 147°-148° C.;

2-[1-(alpha-methoxy-N-4-chlorophenylacetamido)ethyl]-3-oxa-3a lambda$^4$,4-dithio-6-chloro-1,5-diazapentalene, m.p. 169°-171° C.;

2-[1-(alpha-methoxy-N-3,4-dichlorophenylacetamido)methyl]-3-oxa-3a lambda$^4$,4-dithio-6-chloro-1,5-diazapentalene, m.p. glass, E.A. calc % C-36.58, H-2.37, N-9.84, found % C-34.49, H-2.3, N-9.1;

2-[1-(alpha-methoxy-N-3,4-dichlorophenylacetamido)propyl]-3-oxa-3a lambda$^4$,4-dithio-6-chloro-1,5-diazapentalene, m.p. 113°-116° C.;

2-[1-(alpha-ethoxy-N-3,4-dichlorophenylacetamido)ethyl]-3-oxa-3a lambda$^4$,4-dithio-6-chloro-1,5-diazapentalene, m.p. 106°-107° C.;

2-[2-(alpha-t-butoxy-N-3,4-dichlorophenylacetamido)ethyl]-3-oxa-3a lambda$^4$,4-dithio-6-chloro-1,5-diazapentalene;

2-[2-(alpha-fluoro-alpha-methoxy-N-3,4-dichlorophenylacetamido)ethyl]-3-oxa-3a lambda$^4$,4-dithio-6-chloro-1,5-diazapentalene;

2-[2-(alpha-chloro-N-3,4-dichlorophenyl-propionamido)ethyl]-3-oxa-3a lambda$^4$,4-dithio-6-chloro-1,5-diazapentalene;

2-[2-(alpha-methoxy-alpha-fluoro-N-3,4-dichlorophenyl-propionamido)ethyl]-3-oxa-3a lambda$^4$,4-dithio-6-chloro-1,5-diazapentalene;

2-[2-(alpha-bromo-N-3,4-dichlorophenylvaleramido)ethyl]-3-oxa-3a lambda$^4$,4-dithio-6-chloro-1,5-diazapentalene; etc.

Similarly, by following the same procedure but using the corresponding compounds of Preparation E as starting materials the corresponding acryloamido; crotonoamido; but-3-enoamido; beta-methoxycrotonoamido; beta-methoxypropionamido and cyclopropylformamido derivatives of each of the above compounds are preferred, including, for example:

2-[1-(N-3,4-dichlorophenylacryloamido)ethyl]-3-oxa-3a lambda$^4$,4-dithio-6-chloro-1,5-diazapentalene;

2-[1-(N-3,4-dichlorophenylcrotonoamido)ethyl]-3-oxa-3a lambda$^4$,4-dithio-6-chloro-1,5-diazapentalene;

2-[1-(N-3,4-dichlorophenyl-3-butenoamido)ethyl]-3-oxa-3a lambda$^4$,4-dithio-6-chloro-1,5-diazapentalene;

2-[1-(beta-methoxy-N-3,4-dichlorophenylpropionamido)ethyl]-3-oxa-3a lambda$^4$,4-dithio-6-chloro-1,5-diazapentalene;

2-[1-(beta-methoxy-N-3,4-dichlorophenyl-crotonoamido)ethyl]-3-oxa-3a lambda$^4$,4-dithio-6-chloro-1,5-diazapentalene;

2-[1-(N-3,4-dichlorophenylcyclopropylformamido)ethyl]-3-oxa-3a lambda$^4$,4-dithio-6-chloro-1,5-diazapentalene; etc.

EXAMPLE 2

This example illustrates the preparation of the compounds of the invention using sulfur dichloride (SCl$_2$).

In this example 125 ml of sulfur dichloride was added over a 30 min. period to slurry container 248 g of 2-(N-chloroacetyl-N-3,4-dichlorophenylamino)-N-cyanopropionamide and 1 g of 4-dimethylaminopyridine (catalyst) in 1.3 liters of methylene chloride at 24° C. During addition of the sulfur dichloride the temperature of the slurry rose to 32° C. with the rapid evolution of hydrogen chloride and the solids dissolved. The reaction mixture temperature was allowed to rise to 38°C. during the next two hours and was then stirred overnight (about 12 hours). The mixture was then filtered and the recovered solids washed with 400 ml of methylene chloride and then slurried with 400 ml of 1:1 vol methylene chloride and hexane and filtered. The solids were slurried with 300 ml of methylene chloride and combined with one liter of toluene and 150 ml of hexane. The resulting mixture was heated to 90° C. over two hours and then filtered at 70° C. The recovered solids were washed with 100 ml of toluene, at 50° C., and the filtrate recovered and evaporated to dryness. The residue was washed twice with 100 ml of toluene and then slurried with 375 ml of toluene and heated to 80° C. and then cooled to 50° C., resulting in the precipitation of solids. Seventy ml of isopropylamine was added and the mixture allowed to cool to 25° C., over about one hour, and then cooled to 5° C. and then vacuum filtered. The solids were then washed with about 200 ml of isopropylamine and then with 200 ml of hexane and dried under vacuum affording 378.5 g of 2-[-1-(alpha-chloro-N-3,4-dichlorophenylacetamide)ethyl]-3-oxa-3a lambda$^4$,4-dithia-6-chloro-1,5-diazapentalene as a yellow solid. The filtrate was allowed to stand for one day at room temperature resulting in precipitation of solids which were then recovered by filtration affording another 37.5 g of the above product as yellow solids.

Similarly, by following the same procedure but using the appropriate starting materials of Formula A, the compounds prepared in Example 1 are respectively prepared.

EXAMPLE 3

In this example the preventative fungicidal activity against various fungi was determined. The tests were conducted as described below and results summarized in Table 1 hereinbelow. The particular compounds identification numbers and fungi code letters used in Table 1 are identified in Tables A and B, respectively, hereinbelow.

Tomato Late Blight

Compounds of the invention were tested for the control of the Tomato Late Blight organism *Phytophthora infestans conidia* as follows. Five- to six-week-old tomato (variety Bonny Best) seedlings were used. The tomato plants were sprayed with a solution of the test compound in acetone, water and a small amount of a non-ionic emulsifier having concentration of test compound indicated in Table I. The sprayed plants were then inoculated one day later with the organism, placed in an environmental chamber and incubated at 66°-68° F. and 100% relative humidity for at least 16 hours. Following the incubation, the plants were allowed to dry and then were maintained at 60-80% relative humidity for approximately 7 days. The percent disease control provided by a given test compound was based on the percent disease reduction relative to untreated check plants. The compounds giving effective control at the test concentration are tabulated in Table II.

EXAMPLE B

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a solution of the test compound in an acetone-and-water solution containing a small amount of a non-ionic emulsifier having the concentration of test compound indicated in Table I. The sprayed plants were inoculated one day later with the organism, dried and maintained at 60-80% relative humidity for about 12 days. Percent disease control was based on the percent disease development on untreated check plants.

Celery Late Blight

Compounds of the invention were tested for the control of Celery Late Blight using celery (Utah) plants 11 weeks old. The Celery Late Blight organism was *Septoria apii*. The celery plants were sprayed with solutions of the test compound in acetone, water and a nonionic emulsifier. The plants were then inoculated with the organism and placed in an environmental chamber and incubated at 66°-68° F. in 100% relative humidity for an extended period of time (approximately 48 hours). Following the incubation, the plants were allowed to dry and then were maintained at a 60-80% relative humidity for approximately 14 days. The percent disease control provided by a given candidate toxicant is based on the percent disease reduction relative to untreated check plants.

Bean Rust Eradication

Compounds of the invention were tested for the eradication of bean rust, using 16-19 day old pinto bean plants. The pinto bean plants were inoculated with *Uromyces phaseoli typica* in an environmental chamber set for 100° relative humidity and 20°-21° C. After the bean rust has developed, one half of the plants are sprayed with solutions of the test compound in acetone. The percent disease control is determined based on the percent disease control reduction in the plants treated with test solution relative to the untreated plants.

Bean Powdery Mildew

The powdery mildew test was made using bean seedlings (var. Bountiful) with well-developed primary leaves. The pathogen was *Erysiphe polygoni*. The bean seedlings were sprayed with a 250-ppm solution of the test compound in an acetone-water mixture containing a nonionic emulsifier. The treated plants were inoculated one day after spray application of the test compound with the pathogen. The plants were then maintained in a greenhouse at a 60-80% relative humidity and at a temperature of 68°-70° F. The rate of infection on the leaves was made after about 10 days. The percent disease control provided by a given test compound was based on the disease reduction relative to untreated check plants. The compounds of the invention giving effective control at the test concentrations are reported in Table VI.

(It should be noted that in each case the spray solution containing the tests compound is primarily water containing no more than about 5% acetone.)

TABLE A

| Compound ID No. | Compound |
|---|---|
| 1 | 2-[1-(alpha-chloro-N-3,4-dichlorophenylacetamido)ethyl]-3-oxa-3a lambda$^4$,4-dithia-6-chloro-1,5-diazapentalene; |
| 2 | 2-[1-(alpha-chloro-N-3,5-dichlorophenylacetamido)ethyl]-3-oxa-3a lambda$^4$,4-dithio-6-chloro-1,5-diazapentalene; |
| 3 | 2-[1-(alpha-chloro-N-4-chlorophenylacetamido)ethyl]-3-oxa-3a lambda$^4$,4-dithio-6-chloro-1,5-diazapentalene; |
| 4 | 2-[1-(alpha-chloro-N-3-trifluoromethylphenylacetamido)ethyl]-3-oxa-3a lambda$^4$,4-dithio-6-chloro-1,5-diazapentalene; |
| 5 | 2-[1-(alpha-chloro-N-2,6-dimethylphenylacetamido)ethyl]-3-oxa-3a lambda$^4$,4-dithio-6-chloro-1,5-diazapentalene; |
| 6 | 2-[1-(alpha-chloro-N-2,6-diethylphenylacetamido)ethyl]-3-oxa-3a lambda$^4$,4-dithio-6-chloro-1,5-diazapentalene; |
| 7 | 2-[1-(alpha-chloro-N-3,4-dichlorophenylacetamido)methyl]-3-oxa-3a lambda$^4$,4-dithio-6-chloro-1,5-diazapentalene; |

TABLE A-continued

| Compound ID No. | Compound |
|---|---|
| 8 | 2-[1-(alpha, alpha-dichloro-N-3,4-dichlorophenyl-acetamido)ethyl]-3-oxa-3a lambda$^4$,4-dithio-6-chloro-1,5-diazapentalene; |
| 9 | 2-[1-(alpha-methoxy-N-3,4-dichlorophenylacet-amido)ethyl]-3-oxa-3a lambda$^4$,4-dithio-6-chloro-1,5-diazapentalene; |
| 10 | 2-[1-(alpha-methoxy-N-3,5-dichlorophenylacet-amido)ethyl]-3-oxa-3a lambda$^4$,4-dithio-6-chloro-1,5-diazapentalene; |
| 11 | 2-[1-(alpha-methoxy-N-4-chlorophenylacet-amido)ethyl]-3-oxa-3a lambda$^4$,4-dithio-6-chloro-1,5-diazapentalene; |
| 12 | 2-[1-(alpha-methoxy-N-3-trifluoromethylphenyl-acetamido)ethyl]-3-oxo-3a lambda$^4$,4-dithio-6-chloro-1,5-diazapentalene; |
| 13 | 2-[1-(alpha-methoxy-N-2,6-dimethylphenylacet-amido)ethyl]-3-oxa-3a lambda$^4$,4-dithio-6-chloro-1,5-diazapentalene; |
| 14 | 2-[1-(alpha-methoxy-N-2,6-diethylphenylacet-amido)ethyl]-3-oxa-3a lambda $^4$,4-dithio-6-chloro-1,5-diazapentalene; |
| 15 | 2-[1-(alpha-methoxy-N-3,4-dichlorophenylacet-amido)propyl]-3-oxa-3a lambda$^4$,4-dithio-6-chloro-1,5-diazapentalene; |
| 16 | 2-[1-(alpha-ethoxy-N-3,4-dichlorophenylacet-amido)ethyl]-3-oxa-3a lambda$^4$, 4-dithio-6-chloro-1,5-diazapentalene; |
| 17 | 2-[1-(alpha-methoxy-N-2-methyl-6-ethylphenylacet-amido)ethyl]-3-oxa-3a lambda$^4$,4-dithio-6-chloro-1,5-diazapentalene; |
| 18 | 2-[(alpha-methoxy-N-3,4-dichlorophenylacet-amido)methyl]-3-oxa-3a lambda$^4$,4-dithio-6-chloro-1,5-diazapentalene; |

TABLE B

| Fungi Identifying Code Letter | |
|---|---|
| Code Letter | Fungus |
| TLB | Tomato Late Blight |
| TEB | Tomato Early Blight |
| BPM | Bean Powdery Mildew |
| BR | Bean Rust |
| CLB | Celery Leaf Blight |
| GDM | Grape Downy Mildew |

TABLE I

FUNGICIDAL ACTIVITY

| Compound ID No. | Concentration ppm | % Reduction Fungus Identification Letter | | | | | |
|---|---|---|---|---|---|---|---|
| | | TLB | TEB | BPM | BR | CLB | GDM |
| 1 | 250 | 95 | 44 | 0 | 0 | 44 | — |
| 2 | 250 | 50 | 8 | 0 | 13 | — | 95 |
| 3 | 250 | 99 | — | 0 | 0 | 85 | 98 |
| 4 | 250 | 99 | 76 | 0 | 14 | — | 100 |
| 5 | 250 | 57 | 23 | 0 | 21 | — | 74 |
| 6 | 250 | 93 | 89 | 0 | 0 | — | 76 |
| 7 | 250 | 97 | 0 | 0 | 23 | — | — |
| 8 | 250 | 99 | 59 | 0 | 0 | — | 89 |
| 9 | 250 | 100 | 27 | 0 | 0 | — | 99 |
| 10 | 250 | 98 | 0 | 0 | 0 | 26 | 100 |
| 11 | 250 | 100 | 4 | 0 | 0 | — | 100 |
| 12 | 250 | 100 | 45 | 0 | 0 | — | 99 |
| 13 | 250 | 99 | 76 | 35 | — | 68 | 100 |
| 14 | 250 | 88 | 14 | 0 | 0 | — | 94 |
| 15 | 250 | 100 | 4 | 0 | 0 | — | 100 |
| 16 | 250 | 100 | 26 | 0 | 0 | — | 100 |
| 17 | 250 | 99 | 11 | 0 | 0 | 0 | 98 |
| 18 | 250 | 100 | 81 | 0 | 0 | 96 | 98 |

As can be seen from the above table, the tested compounds exhibited excellent preventative action against Tomato Late Blight and Grape Downy Mildew.

EXAMPLE 4

In this example a representative compound (Compound I.D. No. 1) of the invention was tested for preventative, residual, systemic, and eradicant fungicidal activity at different concentrations against Tomato Late Blight and preventative fungicidal activity against Grape Downy Mildew. ED 50s and 90s were calculated, i.e., concentration at which a 50% and 90% reduction in disease over untreated control should occur. The tests were conducted as described below and the results summarized in Tables 2 and 3 respectively hereinbelow. Compound I.D. No. 1 is identified in Table A of Example 3 hereinabove.

Tomato Late Blight

Compound I.D. 1 (Table A) of the invention were tested for the control of the Tomato Late Blight organism *Phytophthora infestans conidia* by both the preventive test and the residual preventative test as follows. Five- to six-week-old tomato (variety Bonny Best) seedlings were used. The tomato plants were sprayed with a solution of the test compound in acetone, water and a small amount of a non-ionic emulsifier having the indicated concentration of test compound. (The spray solution primarily water, i.e., <5% acetone.) The sprayed plants were then inoculated one day later with the organism, placed in an environmental chamber and incubated at 66°-68° F. and 100% relative humidity for at least 16 hours. Following the incubation, the plants were allowed to dry and then were maintained at 60-80% relative humidity for approximately 7 days. The residual preventive test is conducted in the same manner with the exception that the plants were not inoculated until five days after the application of the test compound solution.

The percent disease control provided by a given test compound was based on the percent disease reduction relative to untreated check plants which are inoculated, etc. in the same manner.

Compound I.D. No. 1 of the invention was also tested for their systemic preventive activity. In this test the ground surrounding the tomato plants was drenched with a solution of the test compound, as the indicated concentration, in acetone plus emulsifier. Four days later the plants were inoculated with *Phytophthora infestan conidia*, incubated and allowed to stand in the same manner as described above.

The percent disease control was based on the percent disease reduction relative to untreated control plants which are inoculated etc. in the same manner.

Grape Downy Mildew (*Plasmopara viticola*)

Compound I.D. No. 1 of the invention was tested for both preventive activity against grape downy mildew via both the leaf test and plant test method. In the leaf test, leaves taken from variety Emperor grape plants are placed in petri dishes and sprayed with an acetone solution of the test compound at the indicated concentration and then allowed to dry for 24 hours. In the plant test, actual plants were sprayed with the test solution. The respective test leaves and test plants along with untreated control leaves and plants, respectively were then inoculated with Plasmopara viticola and maintained in a controlled environment at 100% relative humidity and 19°-20° C. for two days and then allowed to dry. The plants were then placed in standing water under a controlled environment temperature of 20°-21°

C. for four days and then removed to another controlled environment at 100% relative humidity for 48 hours and then examined.

The percent control is based on the percent disease control of the treated specimens relative to the control specimens.

$$\% \text{ control} = 100 - \left( \frac{\% \text{ disease in test specimens}}{\% \text{ disease in control specimens}} \times 100 \right)$$

TABLE 2

TOMATO LATE BLIGHT

| Compound ID No.* | Preventative % Reduction Concentration ppm | | | Residual-5-day % Reduction Concentration ppm | | | Systemic % Reduction Concentration ppm | | | Eradicant % Reduction Concentration ppm | | |
|---|---|---|---|---|---|---|---|---|---|---|---|---|
| | 100 | 40 | 16 | 55 | 40 | 16 | 200 | 80 | 32 | 250 | 100 | 40 |
| 1 | 96 | 77 | 50 | 55 | 40 | 27 | 0 | 0 | 34 | 58 | 0 | 8 |
| ED 50/90 ppm | 18/68 | | | 76/- | | | | | | 217/- | | |

*See Table A of Example 1 above.

TABLE 3

GRAPE DOWNY MILDEW

| Compound ID No. | Preventative Leaf Test % Reduction Concentration ppm | | | Preventative Plant Test % Reduction Concentration ppm | |
|---|---|---|---|---|---|
| | 100 | 40 | 16 | 250 | 100 |
| 1 | 98 | 45 | 0 | 100 | 100 |
| ED 50/90 ppm | 42/71 | | | | |

As can be seen from the above results the Compound I.D. No. 1 exhibited excellent preventative activity moderate residual preventative activity after 5 days and some eradicant activity.

EXAMPLE 5

In this example a number of representative compounds of the invention were examined for preventative Tomato Late Blight activity at different concentrations via the same procedure as described in Example 3 hereinabove. Percent control was determined in the same manner as in Example 3, i.e.:

$$\% \text{ Control} = 100 - \left( \frac{\% \text{ disease (i.e. lesions) in treated plants}}{\% \text{ disease (i.e. lesions) in untreated plants}} \right)$$

The compounds tested are identified in Table A of Example 3 hereinabove and the results summarized in Table 4 hereinbelow.

TABLE 4

PREVENTATIVE ACTIVITY TOMATO LATE BLIGHT

| Compound ID No. | Concentration ppm | | |
|---|---|---|---|
| | 250 | 100 | 40 |
| 1 | 98 | 89 | 93 |
| 2 | 89 | 83 | 81 |
| 3 | 73 | 98 | 98 |
| 4 | 95 | 95 | 86 |
| 5 | 86 | 73 | 77 |
| 6 | 62 | 67 | 55 |
| 7 | 83 | 83 | 86 |
| 8 | 86 | 89 | 86 |
| 9 | 99 | 98 | 93 |
| 10 | 97 | 98 | 97 |
| 11 | 100 | 97 | 99 |

TABLE 4-continued

PREVENTATIVE ACTIVITY TOMATO LATE BLIGHT

| Compound ID No. | Concentration ppm | | |
|---|---|---|---|
| | 250 | 100 | 40 |
| 12 | 98 | 97 | 99 |
| 13 | 97 | 93 | 91 |
| 14 | 99 | 98 | 96 |
| 15 | 98 | 94 | 97 |
| 16 | 96 | 99 | 74 |

As can be seen from the above table all of the compounds exhibited excellent preventative activity against Tomato Late Blight in this test.

EXAMPLE 6

In this example a representative compound of Formula 1 (i.e. Compound I.D. No. 1, Table A) was tested for herbicidal properties.

PRE-EMERGENT HERBICIDE TEST

Pre-emergence herbicidal activity was determined in the following manner.

An acetone solution of the imidazolidinedione test compound was prepared by mixing 750 mg of the test compound, 220 mg of a nonionic surfactant and 25 ml of acetone. This solution was added to approximately 125 ml of water containing 156 mg of surfactant.

Seeds of the test vegetation were planted in a pot of soil and the imidazolidinedione test solution was sprayed uniformly onto the soil surface at a dose of 27 mcgm/c$^2$. The pot was watered and placed in a greenhouse. The pot was watered intermittently and was observed for seedling emergence, health of the emerging seedlings, etc., for a 3-week period. At the end of this period, the herbicidal effectiveness of the imidazolidinedione test compound was rated based on the physiological observations. A 0-to-100 scale was used, 0-representing no phytotoxicity and 100 representing complete kill. The results of these tests are summarized in Table 5, hereinbelow.

POST-EMERGENT TEST

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 27 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests are summarized in Table 6.

The compound tested is identified in Table A of Example 3 hereinabove and the results of these tests are summarized in Table 5 with respect to pre-emergent herbicidal activity and Table 6 with respect to post-emergent herbicidal activity. As can be seen from these tables the compound did not exhibit any herbicidal activity.

TABLE 5

Pre-Emergence Herbicidal Activity

| Compound ID No. | Concentration Micrograms Per cm² | Broad-Leaf Plants % kill | | | Grasses % kill | | | Crops % kill | |
|---|---|---|---|---|---|---|---|---|---|
| | | Mustard | Pigweed | Lambsquarter | W. Oats | Watergrass | Crabgrass | Soybean | Rice |
| 1 | 27 | 0 | 0 | 0 | 0 | 0 | 0 | 0 | 0 |

TABLE 6

Post-Emergence Herbicidal Activity

| Compound ID No. | Concentration Micrograms Per cm² | Broad-Leaf Plants % kill | | | Grasses % kill | | | Crops % kill | |
|---|---|---|---|---|---|---|---|---|---|
| | | Mustard | Pigweed | Lambsquarter | W. Oats | Watergrass | Crabgrass | Soybean | Rice |
| 1 | 27 | 0 | 0 | 0 | 0 | 0 | 0 | 0 | 0 |

As can be seen from the above results, the Compound I.D. No. 1 did not exhibit any herbicidal activity at the dosage tested and thus can be safely applied to plants as fungicides.

Obviously, many modifications and variations of the invention, described hereinabove and below in the claims, can be made without departing from the essence and nope thereof.

What is claimed is:

1. A compound selected from the group having the formula

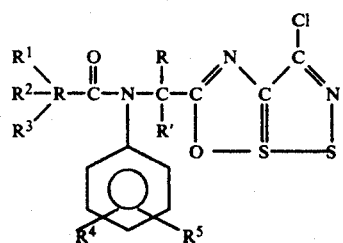

wherein
R and R' are independently selected from the group consisting of hydrogen and lower alkyl;
R¹ is hydrogen or lower alkyl;
R² and R³ are independently selected from the group consisting of hydrogen, lower alkenyl, hydroxy, lower hydroxyalkenyl, lower alkoxy, lower alkoxyalkyl, lower alkoxyalkenyl, lower alkylthio, halogen, and haloalkyl having 1 through 3 carbon atoms and 1 through 4 halo atoms; or R² and R³ together are lower alkylidiene or lower alkoxyalkylidiene; or R² and R³ together with the carbon atom to which they are joined form a cycloalkyl group having from 3 through 7 carbon atoms; and R⁴ and R⁵ are independently selected from the group consisting of hydrogen, lower alkyl, lower alkoxy, halogen, haloalkyl having 1 through 2 carbon atoms and from 1 through 4 halo atoms, nitro, cyano, and di(lower alkyl)amino; and compatible salts thereof.

2. The compound of claim 1 wherein one of R or R' is hydrogen or methyl and the other is hydrogen, methyl, or ethyl.

3. The compound of claim 1 wherein R¹ is hydrogen, methyl or ethyl.

4. The compound of claim 1 wherein one of R² or R³ is hydrogen and the other is selected from the group consisting of chloro, methoxy, and ethoxy.

5. The compound of claim 4 wherein R¹ and R² are each hydrogen.

6. The compound of claim 1 wherein R⁴ and R⁵ are independently selected from the group consisting of chloro, methyl, ethyl, and trifluoromethyl.

7. The compound of claim 6 wherein R⁴ is chloro and R⁵ is chloro.

8. The compound of claim 6 wherein one of R or R' is hydrogen or methyl and the other is hydrogen, methyl or ethyl; R¹ is hydrogen or methyl and one of R² or R³ is hydrogen or methyl and the other is selected from the group consisting of chloro, methoxy and ethoxy.

9. The compound of claim 8 wherein one of R or R' is hydrogen and the other is methyl.

10. The compound of claim 1 wherein one of R or R' is hydrogen and the other hydrogen, methyl or ethyl, R¹ is hydrogen; R² is hydrogen or chloro; R³ is chloro, methoxy or ethoxy; R⁴ is hydrogen, chloro, trifluoromethyl, methyl or ethyl, and R⁵ is chloro, trifluoromethyl, methyl or ethyl.

11. The compound of claim 10 wherein one of R or R' is hydrogen and the other is methyl.

12. The compound of claim 10 wherein R² is hydrogen.

13. The compound of claim 12 wherein R⁴ is hydrogen and R⁵ is chloro or trifluoromethyl.

14. The compound of claim 12 wherein R⁴ is chloro, methyl or ethyl and R⁵ is chloro, methyl or ethyl.

15. The compound of claim 1 wherein said compound is 2-(1-(alpha-chloro-N-3,4-dichlorophenylacetamido)ethyl)-3-oxa-3a lambda⁴,4-dithia-6-chloro-1,5-diazapentalene.

16. The compound of claim 1 wherein said compound is 2-(1-alpha-methoxy-N-3,4-dichlorophenylacetamido)ethyl)-3-oxa-3a lambda⁴,4-dithia-6-chloro-1,5-diazapentalene.

17. The compound of claim 1 wherein said compound is 2-(1-(alpha-chloro-N-2,6-dimethylphenylacetamido)ethyl)-3-oxa-3a lambda$^4$,4-dithia-6-chloro-1,5-diazapentalene.

18. The compound of claim 1 wherein said compound is 2-(1-(alpha-methoxy-N-2,6-dimethylphenylacetamido)ethyl)-3-oxa-3a lambda$^4$,4-dithia-6-chloro-1,5-diazapentalene.

19. The compound of claim 1 wherein said compound is 2-(1-(alpha-chloro-N-3-trifluoromethylphenylacetamido)ethyl)-3-oxa-3a lambda$^4$,4-dithia-6-chloro-1,5-diazapentalene.

20. The compound of claim 1 wherein said compound is 2-(1-(alpha-methoxy-N-3-trifluoromethylphenylacetamido)ethyl)-3-oxa-3a lambda$^4$,4-dithia-6-chloro-1,5-diazapentalene.

21. The compound of claim 1 wherein said compound is 2-(1-(alpha-methoxy-N-3,4-dichlorophenylacetamido)propyl)-3-oxa-3a lambda$^4$,4-dithia-6-chloro-1,5-diazapentalene.

22. The compound of claim 1 wherein said compound is 2-(1-(alpha-ethoxy-N-3,4-dichlorophenylacetamido)ethyl)-3-oxa-3a lambda$^4$,4-dithia-6-chloro-1,5-diazapentalene.

23. The compound of claim 1 wherein said compound is 2-(1-(alpha-chloro-N-4-chlorophenylacetamido)ethyl)-3-oxa-3a lambda$^4$,4-dithio-6-chloro-1,5-diazapentalene.

24. The compound of claim 1 wherein said compound is 2-(1-(alpha-methoxy-N-4-chlorophenylacetamido)ethyl)-3-oxa-3a lambda$^4$,4-dithio-6-chloro-1,5-diazapentalene.

25. The compound of claim 1 wherein said compound is 2-(1-(alpha-methoxy-N-2,6-diethylphenylacetamido)ethyl)-3-oxa-3a lambda$^4$,4-dithio-6-chloro-1,5-diazapentalene.

26. The compound of claim 1 wherein said compound is 2-(1-(alpha-ethoxy-N-3,5-dichlorophenylacetamido)ethyl)-3-oxa-3a lambda$^4$,4-dithio-6-chloro-1,5-diazapentalene.

27. A fungicidal composition comprising an amount of the compound of claim 1 effective to prevent or arrest fungi and a compatible inert carrier.

28. A method of controlling tomato late blight or grape downy mildew diseases which comprises applying an amount of the compound of claim 1 effective to prevent or arrest said diseases to vegetation subject to such diseases.

* * * * *

UNITED STATES PATENT AND TRADEMARK OFFICE
CERTIFICATE OF CORRECTION

PATENT NO. : 4,260,624
DATED : April 7, 1981
INVENTOR(S) : Joseph E. Moore

It is certified that error appears in the above-identified patent and that said Letters Patent are hereby corrected as shown below:

Col. 2 of the Preamble Page, first line following formula in the Abstract, "hydroxy" should read --hydrogen--.

Signed and Sealed this

Fifteenth Day of December 1981

|SEAL|

Attest:

GERALD J. MOSSINGHOFF

Attesting Officer     Commissioner of Patents and Trademarks